(12) United States Patent
Lutje Spelberg et al.

(10) Patent No.: US 6,387,668 B1
(45) Date of Patent: May 14, 2002

(54) ENANTIOSELECTIVE EPOXIDE HYDROLASES AND GENES ENCODING THESE

(75) Inventors: Jeffrey Harald Lutje Spelberg; Rick Rink, both of Groningen; Richard Morrison Kellogg, Haren; Dirk Barend Janssen, Roden, all of (NL)

(73) Assignee: Rijksuniversiteit Groningen, Groningen (NL)

( * ) Notice: Subject to any disclaimer, the term of this patent is extended or adjusted under 35 U.S.C. 154(b) by 0 days.

(21) Appl. No.: 09/424,349

(22) PCT Filed: May 20, 1998

(86) PCT No.: PCT/NL98/00290

§ 371 Date: Feb. 23, 2000

§ 102(e) Date: Feb. 23, 2000

(87) PCT Pub. No.: WO98/53081

PCT Pub. Date: Nov. 26, 1998

(30) Foreign Application Priority Data

May 21, 1997 (EP) .............................. 97201515

(51) Int. Cl.$^7$ .............................. C12P 2/02; C12N 9/14
(52) U.S. Cl. ................. 435/155; 435/195; 435/280
(58) Field of Search ................. 435/195, 280, 435/155

(56) References Cited

U.S. PATENT DOCUMENTS 5,445,956 A * 8/1995 Hammock et al. .......... 435/195

FOREIGN PATENT DOCUMENTS

| WO | 96/12818 | * | 5/1996 |
| WO | 98/53081 | * | 11/1998 |

OTHER PUBLICATIONS

Mischitz, M. et al. (1995) Tetrahedron. Asymmetry 6(6), 1261–1272.*
Pedragosa–Moreau. et al. (1996) J. Org. Chem. 61, 7402–7407.*
Rink, R., et al. (1997) J. Biol. Chem. 272(23), 14650–14657.*

* cited by examiner

Primary Examiner—Charles L. Patterson, Jr.
(74) Attorney, Agent, or Firm—Michaelson & Wallace; Peter L. Michaelson; Edward M. Fink

(57) ABSTRACT

An isolated microorganism capable of selectively degrading epichlorohydrin or related halopropanol compounds is described. The microorganism is a representative of Agrobacterium spp and comprises a nucleic acid molecule encoding a polypeptide having enantioselective epoxide hydrolase activity.

11 Claims, 6 Drawing Sheets

```
atgactatcagaagacccgaagactttaaacactacgaagtgcagttaccagacgtgaaa  60
 M  T  I  R  R  P  E  D  F  K  H  Y  E  V  Q  L  P  D  V  K   20 atccactacgtccgcgagggagcgggtccgacactgttgctgttgcacggctggcccggg 120
 I  H  Y  V  R  E  G  A  G  P  T  L  L  L  H  G  W  P  G     40 ttctggtgggagtggagcaaggtcataggcccgctcgcagagcactacgatgtcattgtt 180
 F  W  W  E  W  S  K  V  I  G  P  L  A  E  H  Y  D  V  I  V  60 cccgacctgcgcggcttcggtgactccgaaaagccggacttaaacgacttgtccaagtac 240
 P  D  L  R  G  F  G  D  S  E  K  P  D  L  N  D  L  S  K  Y  80 tcgctcgacaaagcggccgacgacaagcagcccttctcgacgcactagggattgaaaag 300
 S  L  D  K  A  A  D  D  Q  A  A  L  L  D  A  L  G  I  E  K 100 gcgtacgtcgttggccatgacttcgcggccatcgtcctccataaattcattcgaaagtac 360
 A  Y  V  V  G  H  D  F  A  A  I  V  L  H  K  F  I  R  K  Y 120 agcgatcgagtcatcaaagcagcgatctttgatcctatccagcccgactttgggccggtc 420
 S  D  R  V  I  K  A  A  I  F  D  P  I  Q  P  D  F  G  P  V 140 tacttcggcttggggcacgtccacgagtcgtggtactcgcaattccatcaactagatatg 480
 Y  F  G  L  G  H  V  H  E  S  W  Y  S  Q  F  H  Q  L  D  M 160 gccgttgaggtcgtgggctcgagtcgcgaggtgtgcaagaagtacttcaaacacttcttc 540
 A  V  E  V  V  G  S  S  R  E  V  C  K  K  Y  F  K  H  F  F 180
```

FIG. 1A

```
gatcactggtcataccgggatgagttgctcactgaggaagaacttgaggttcacgtcgat  600
 D  H  W  S  Y  R  D  E  L  L  T  E  E  E  L  E  V  H  V  D  200 aactgtatgaagcctgacaacattcacggaggcttcaactactatcgtgccaacataagg  660
 N  C  M  K  P  D  N  I  H  G  G  F  N  Y  Y  R  A  N  I  R  220 cccgatgccgctctgtggacagacctcgatcatacgatgagcgaccttccagtaacaatg  720
 P  D  A  A  L  W  T  D  L  D  H  T  M  S  D  L  P  V  T  M  240 atatggggtttgggagatacttgcgtgccctatgctccactcattgaattcgttcctaag  780
 I  W  G  L  G [D] T  C  V  P  Y  A  P  L  I  E  F  V  P  K  260 tactattcgaactatacgatggagacgatcgaagactgcggtcacttcttgatggtcgaa  840
 Y  Y  S  N  Y  T  M  E  T  I  E  D  C  G [H] F  L  M  V  E  280 aaacctgaaattgccatcgatcgaatcaaaaccgcgttccgctga                 885
 K  P  E  I  A  I  D  R  I  K  T  A  F  R  -                 294
```

| EPOXIDE | %E.E | YIELD(%) OF THE REMAINING ENANTIOMER | ABS. CONF. |
|---|---|---|---|
| 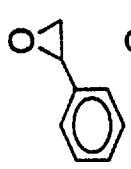 | 99 | 65 | (S)[a] |
| 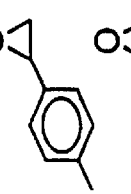 | >99[c] | 72 | (S)[b] |
| 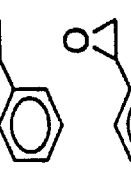 | >99 | 54 | (?)[b] |
| 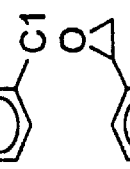 | >99[c] | 70 | (+)[b] |
| 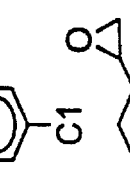 | >99[c] | 54 | (S)[a] |
| 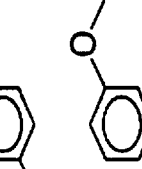 | >99[c] | 67 | (S)[b] |
|  | 99 | 55 | (R)[b] |
Fig. 5

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 885 base pairs
      (B) TYPE: nucleic acid
      (C) STRANDEDNESS: unknown
      (D) TOPOLOGY: unknown -continued (ii) MOLECULE TYPE: DNA (genomic)

(iii) HYPOTHETICAL: NO (xi) SEQUENCE DESCRIPTION: SEQ ID NO: 1:

```
ATGACTATCA AAGACCCGA AGACTTTAAA CACTACGAAG TGCAGTTACC AGACGTGAAA      60
ATCCACTACG TCCGCGAGGG AGCGGGTCCG ACACTGTTGC TGTTGCACGG CTGGCCCGGG    120
TTCTGGTGGG AGTGGAGCAA GGTCATAGGC CCGCTCGCAG AGCACTACGA TGTCATTGTT    180
CCCGACCTGC GCGGCTTCGG TGACTCCGAA AAGCCGGACT TAAACGACTT GTCCAAGTAC    240
TCGCTCGACA AAGCGGCCGA CGACCAAGCA GCCCTTCTCG ACGCACTAGG GATTGAAAAG    300
GCGTACGTCG TTGGCCATGA CTTCGCGGCC ATCGTCCTCC ATAAATTCAT TCGAAAGTAC    360
AGCGATCGAG TCATCAAAGC AGCGATCTTT GATCCTATCC AGCCCGACTT TGGGCCGGTC    420
TACTTCGGCT TGGGGCACGT CCACGAGTCG TGGTACTCGC AATTCCATCA ACTAGATATG    480
GCCGTTGAGG TCGTGGGCTC GAGTCGCGAG GTGTGCAAGA AGTACTTCAA ACACTTCTTC    540
GATCACTGGT CATACCGGGA TGAGTTGCTC ACTGAGGAAG AACTTGAGGT TCACGTCGAT    600
AACTGTATGA AGCCTGACAA CATTCACGGA GGCTTCAACT ACTATCGTGC CAACATAAGG    660
CCCGATGCCG CTCTGTGGAC AGACCTCGAT CATACGATGA GCGACCTTCC AGTAACAATG    720
ATATGGGGTT TGGGAGATAC TTGCGTGCCC TATGCTCCAC TCATTGAATT CGTTCCTAAG    780
TACTATTCGA ACTATACGAT GGAGACGATC GAAGACTGCG GTCACTTCTT GATGGTCGAA    840
AAACCTGAAA TTGCCATCGA TCGAATCAAA ACCGCGTTCC GCTGA                    885
```

(2) INFORMATION FOR SEQ ID NO: 2:

(i) SEQUENCE CHARACTERISTICS:
        (A) LENGTH: 294 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 2:

```
Met Thr Ile Arg Arg Pro Glu Asp Phe Lys His Tyr Glu Val Gln Leu
1               5                   10                  15

Pro Asp Val Lys Ile His Tyr Val Arg Glu Gly Ala Gly Pro Thr Leu
            20                  25                  30

Leu Leu Leu His Gly Trp Pro Gly Phe Trp Trp Glu Trp Ser Lys Val
        35                  40                  45

Ile Gly Pro Leu Ala Glu His Tyr Asp Val Ile Val Pro Asp Leu Arg
    50                  55                  60

Gly Phe Gly Asp Ser Glu Lys Pro Asp Leu Asn Asp Leu Ser Lys Tyr
65                  70                  75                  80

Ser Leu Asp Lys Ala Ala Asp Asp Gln Ala Ala Leu Leu Asp Ala Leu
                85                  90                  95

Gly Ile Glu Lys Ala Tyr Val Val Gly His Asp Phe Ala Ala Ile Val
            100                 105                 110

Leu His Lys Phe Ile Arg Lys Tyr Ser Asp Arg Val Ile Lys Ala Ala
        115                 120                 125

Ile Phe Asp Pro Ile Gln Pro Asp Phe Gly Pro Val Tyr Phe Gly Leu
    130                 135                 140

Gly His Val His Glu Ser Trp Tyr Ser Gln Phe His Gln Leu Asp Met
```

-continued

```
145                 150                 155                 160
Ala Val Glu Val Val Gly Ser Ser Arg Glu Val Cys Lys Lys Tyr Phe
                165                 170                 175

Lys His Phe Phe Asp His Trp Ser Tyr Arg Asp Glu Leu Leu Thr Glu
                180                 185                 190

Glu Glu Leu Glu Val His Val Asp Asn Cys Met Lys Pro Asp Asn Ile
                195                 200                 205

His Gly Gly Phe Asn Tyr Tyr Arg Ala Asn Ile Arg Pro Asp Ala Ala
                210                 215                 220

Leu Trp Thr Asp Leu Asp His Thr Met Ser Asp Leu Pro Val Thr Met
225                 230                 235                 240

Ile Trp Gly Leu Gly Asp Thr Cys Val Pro Tyr Ala Pro Leu Ile Glu
                245                 250                 255

Phe Val Pro Lys Tyr Tyr Ser Asn Tyr Thr Met Glu Thr Ile Glu Asp
                260                 265                 270

Cys Gly His Phe Leu Met Val Glu Lys Pro Glu Ile Ala Ile Asp Arg
                275                 280                 285

Ile Lys Thr Ala Phe Arg
        290
```

(2) INFORMATION FOR SEQ ID NO: 3:

(i) SEQUENCE CHARACTERISTICS:
        (A) LENGTH: 294 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 3:

```
Met Asp Phe Pro Gly Phe Lys Asn Ser Thr Val Thr Val Asp Gly Val
1                   5                   10                  15

Asp Ile Ala Tyr Thr Val Ser Gly Glu Gly Pro Pro Val Leu Met Leu
                20                  25                  30

His Gly Phe Pro Gln Asn Arg Ala Met Trp Ala Arg Val Ala Pro Gln
                35                  40                  45

Leu Ala Glu His His Thr Val Val Cys Ala Asp Leu Arg Gly Tyr Gly
                50                  55                  60

Asp Ser Asp Lys Pro Lys Cys Leu Pro Asp Arg Ser Asn Tyr Ser Phe
65                  70                  75                  80

Arg Thr Phe Ala His Asp Gln Leu Cys Val Met Arg His Leu Gly Phe
                85                  90                  95

Glu Arg Phe His Leu Val Gly His Asp Arg Gly Gly Arg Thr Gly His
                100                 105                 110

Arg Met Ala Leu Asp His Pro Glu Ala Val Leu Ser Leu Thr Val Met
                115                 120                 125

Asp Ile Val Pro Thr Tyr Ala Met Phe Met Asn Thr Asn Arg Leu Val
                130                 135                 140

Ala Ala Ser Tyr Trp His Trp Tyr Phe Leu Gln Gln Pro Glu Pro Phe
145                 150                 155                 160

Pro Glu His Met Ile Gly Gln Asp Pro Asp Phe Phe Tyr Glu Thr Cys
                165                 170                 175

Leu Phe Gly Trp Gly Ala Thr Lys Val Ser Asp Phe Asp Gln Gln Met
                180                 185                 190
```

```
Leu Asn Ala Tyr Arg Glu Ser Trp Arg Asn Pro Ala Met Ile His Gly
        195                 200                 205

Ser Cys Ser Asp Tyr Arg Ala Ala Thr Ile Asp Leu Glu His Asp
    210                 215                 220

Ser Ala Asp Ile Gln Arg Lys Val Glu Cys Pro Thr Leu Val Phe Tyr
225                 230                 235                 240

Gly Ser Lys Gly Gln Met Gly Gln Leu Phe Asp Ile Pro Ala Glu Trp
                245                 250                 255

Ala Lys Arg Cys Asn Asn Thr Thr Asn Ala Ser Leu Pro Gly Gly His
            260                 265                 270

Phe Phe Val Asp Gln Phe Pro Ala Glu Thr Ser Glu Ile Leu Leu Lys
        275                 280                 285

Phe Leu Ala Arg Asn Gly
        290
```

(2) INFORMATION FOR SEQ ID NO: 4:

(i) SEQUENCE CHARACTERISTICS:
       (A) LENGTH: 322 amino acids
       (B) TYPE: amino acid
       (C) STRANDEDNESS: unknown
       (D) TOPOLOGY: unknown (ii) MOLECULE TYPE: peptide (iii) HYPOTHETICAL: NO (xi) SEQUENCE DESCRIPTION: SEQ ID NO: 4:

```
Met Glu Lys Ile Glu His Lys Met Val Ala Val Asn Gly Leu Asn Met
1               5                   10                  15

His Leu Ala Glu Leu Gly Glu Gly Pro Thr Ile Leu Phe Ile His Gly
            20                  25                  30

Phe Pro Glu Leu Trp Tyr Ser Trp Arg His Gln Met Val Tyr Leu Ala
        35                  40                  45

Glu Arg Gly Tyr Arg Ala Val Ala Pro Asp Leu Arg Gly Tyr Gly Asp
    50                  55                  60

Thr Thr Gly Ala Pro Leu Asn Asp Pro Ser Lys Phe Ser Ile Leu His
65                  70                  75                  80

Leu Val Gly Asp Val Val Ala Leu Leu Glu Ala Ile Ala Pro Asn Glu
                85                  90                  95

Glu Lys Val Phe Val Val Ala His Asp Trp Gly Ala Leu Ile Ala Trp
            100                 105                 110

His Leu Cys Leu Phe Arg Pro Asp Lys Val Lys Ala Leu Val Asn Leu
        115                 120                 125

Ser Val His Phe Ser Lys Arg Asn Pro Lys Met Asn Val Val Glu Gly
    130                 135                 140

Leu Lys Ala Ile Tyr Gly Glu Asp His Tyr Ile Ser Arg Phe Gln Val
145                 150                 155                 160

Pro Gly Glu Ile Glu Ala Glu Phe Ala Pro Ile Gly Ala Lys Ser Val
                165                 170                 175

Leu Lys Lys Ile Leu Thr Tyr Arg Asp Pro Ala Pro Phe Tyr Phe Pro
            180                 185                 190

Lys Gly Lys Gly Leu Glu Ala Ile Pro Asp Ala Pro Val Ala Leu Ser
        195                 200                 205

Ser Trp Leu Ser Glu Glu Glu Leu Asp Tyr Tyr Ala Asn Lys Phe Glu
    210                 215                 220
```

```
Gln Thr Gly Phe Thr Gly Ala Val Asn Tyr Tyr Arg Ala Leu Pro Ile
225                 230                 235                 240

Asn Trp Glu Leu Thr Ala Pro Trp Thr Gly Ala Gln Val Lys Val Pro
                245                 250                 255

Thr Lys Phe Ile Val Gly Glu Phe Asp Leu Val Tyr His Ile Pro Gly
            260                 265                 270

Ala Lys Glu Tyr Ile His Asn Gly Gly Phe Lys Lys Asp Val Pro Leu
            275                 280                 285

Leu Glu Glu Val Val Val Leu Glu Gly Ala Ala His Phe Val Ser Gln
        290                 295                 300

Glu Arg Pro His Glu Ile Ser Lys His Ile Tyr Asp Phe Ile Gln Lys
305                 310                 315                 320

Phe Met (2) INFORMATION FOR SEQ ID NO: 5:

(i) SEQUENCE CHARACTERISTICS:
        (A) LENGTH: 312 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 5:

Thr Val Lys Pro Arg Val Arg Leu His Phe Val Glu Leu Gly Trp Pro
1               5                   10                  15

Ala Val Cys Leu Cys His Gly Phe Pro Glu Ser Trp Tyr Ser Trp Arg
            20                  25                  30

Tyr Asp Ile Pro Ala Leu Ala Gln Ala Gly Tyr Arg Val Leu Ala Met
            35                  40                  45

Asp Met Lys Gly Tyr Gly Glu Ser Ser Ala Pro Pro Glu Ile Glu Glu
50                  55                  60

Tyr Cys Met Glu Val Leu Cys Lys Glu Met Val Thr Phe Leu Asp Lys
65                  70                  75                  80

Leu Gly Leu Ser Gln Ala Val Phe Ile Gly His Asp Trp Gly Gly Met
                85                  90                  95

Leu Val Trp Tyr Met Ala Leu Phe Tyr Pro Glu Arg Val Arg Ala Val
                100                 105                 110

Ala Ser Leu Asn Thr Pro Phe Ile Pro Ala Asn Pro Asn Met Ser Pro
            115                 120                 125

Leu Glu Ser Ile Lys Ala Asn Pro Val Phe Asp Tyr Gln Leu Tyr Phe
        130                 135                 140

Gln Glu Pro Gly Val Ala Glu Ala Glu Leu Glu Gln Asn Leu Ser Arg
145                 150                 155                 160

Thr Phe Lys Ser Leu Phe Arg Ala Ser Asp Glu Ser Val Leu Ser Met
                165                 170                 175

His Lys Val Cys Glu Ala Gly Gly Leu Phe Val Asn Ser Pro Glu Glu
            180                 185                 190

Pro Ser Leu Ser Arg Met Val Thr Glu Glu Glu Ile Gln Phe Tyr Val
            195                 200                 205

Gln Gln Phe Lys Lys Ser Gly Phe Arg Gly Pro Leu Asn Trp Tyr Arg
        210                 215                 220

Asn Met Glu Arg Asn Trp Lys Trp Ala Cys Lys Ser Leu Gly Arg Lys
225                 230                 235                 240
```

```
Ile Leu Ile Pro Ala Leu Met Val Thr Ala Glu Lys Asp Phe Val Leu
                245                 250                 255

Val Pro Gln Met Ser Gln His Met Glu Asp Trp Ile Pro His Leu Lys
            260                 265                 270

Arg Gly His Ile Glu Asp Cys Gly His Trp Thr Gln Met Asp Lys Pro
            275                 280                 285

Thr Glu Val Asn Gln Ile Leu Ile Lys Trp Leu Asp Ser Asp Ala Arg
            290                 295                 300

Asn Pro Pro Val Val Ser Lys Met
305                 310
```

(2) INFORMATION FOR SEQ ID NO: 6:

(i) SEQUENCE CHARACTERISTICS:
        (A) LENGTH: 277 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 6:

```
Pro Phe Ile Thr Val Gly Gln Glu Asn Ser Thr Ser Ile Asp Leu Tyr
1               5                   10                  15

Tyr Glu Asp His Gly Thr Gly Gln Pro Val Val Leu Ile His Gly Phe
            20                  25                  30

Pro Leu Ser Gly His Ser Trp Glu Arg Gln Ser Ala Ala Leu Leu Asp
            35                  40                  45

Ala Gly Tyr Arg Val Ile Thr Tyr Asp Arg Arg Gly Phe Gly Gln Ser
    50                  55                  60

Ser Gln Pro Thr Thr Gly Tyr Asp Tyr Asp Thr Phe Ala Ala Asp Leu
65                  70                  75                  80

Asn Thr Val Leu Glu Thr Leu Asp Leu Gln Asp Ala Val Leu Val Gly
                85                  90                  95

Phe Ser Met Gly Thr Gly Glu Val Ala Arg Tyr Val Ser Ser Tyr Gly
            100                 105                 110

Thr Ala Arg Ile Ala Lys Val Ala Phe Leu Ala Ser Leu Glu Pro Phe
            115                 120                 125

Leu Leu Lys Thr Asp Asp Asn Pro Asp Gly Ala Ala Pro Gln Glu Phe
            130                 135                 140

Phe Asp Gly Ile Val Ala Ala Val Lys Ala Asp Arg Tyr Ala Phe Tyr
145                 150                 155                 160

Thr Gly Phe Phe Asn Asp Phe Tyr Asn Leu Asp Glu Asn Leu Gly Thr
                165                 170                 175

Arg Ile Ser Glu Glu Ala Val Arg Asn Ser Trp Asn Thr Ala Ala Ser
            180                 185                 190

Gly Gly Phe Phe Ala Ala Ala Ala Pro Thr Thr Trp Tyr Thr Asp
            195                 200                 205

Phe Arg Ala Asp Ile Pro Arg Ile Asp Val Pro Ala Leu Ile Leu His
            210                 215                 220

Gly Thr Gly Asp Arg Thr Leu Pro Ile Glu Asn Thr Ala Arg Val Phe
225                 230                 235                 240

His Lys Ala Leu Pro Ser Ala Glu Tyr Val Glu Val Glu Gly Ala Pro
                245                 250                 255
```

His Gly Leu Leu Trp Thr His Ala Glu Glu Val Asn Thr Ala Leu Leu
            260                 265                 270

Ala Phe Leu Ala Lys
            275

(2) INFORMATION FOR SEQ ID NO: 7:

(i) SEQUENCE CHARACTERISTICS:
        (A) LENGTH: 298 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 7:

Ser Asn Leu Asp Gln Tyr Pro Phe Ser Pro Asn Tyr Leu Asp Asp Leu
1               5                   10                  15

Pro Gly Tyr Pro Gly Leu Arg Ala His Tyr Leu Asp Glu Gly Asn Ser
            20                  25                  30

Asp Ala Glu Asp Val Phe Leu Cys Leu His Gly Glu Pro Thr Trp Ser
            35                  40                  45

Tyr Leu Tyr Arg Lys Met Ile Pro Val Phe Ala Glu Ser Gly Ala Arg
50                  55                  60

Val Ile Ala Pro Asp Phe Phe Gly Phe Gly Lys Ser Asp Lys Pro Val
65                  70                  75                  80

Asp Glu Glu Asp Tyr Thr Phe Glu Phe His Arg Asn Phe Leu Leu Ala
            85                  90                  95

Leu Ile Glu Arg Leu Asp Leu Arg Asn Ile Thr Leu Val Val Gln Asp
            100                 105                 110

Trp Gly Gly Phe Leu Gly Leu Thr Leu Pro Met Ala Asp Pro Ser Arg
            115                 120                 125

Phe Lys Arg Leu Ile Ile Met Asn Ala Cys Leu Met Thr Asp Pro Val
            130                 135                 140

Thr Gln Pro Ala Phe Ser Ala Phe Val Thr Gln Pro Ala Asp Gly Phe
145                 150                 155                 160

Thr Ala Trp Lys Tyr Asp Leu Val Thr Pro Ser Asp Leu Arg Leu Asp
            165                 170                 175

Gln Phe Met Lys Arg Trp Ala Pro Thr Leu Thr Glu Ala Glu Ala Ser
            180                 185                 190

Ala Tyr Ala Ala Pro Phe Pro Asp Thr Ser Tyr Gln Ala Gly Val Arg
            195                 200                 205

Lys Phe Pro Lys Met Val Ala Gln Arg Asp Gln Ala Cys Ile Asp Ile
            210                 215                 220

Ser Thr Glu Ala Ile Ser Phe Trp Gln Asn Asp Trp Asn Gly Gln Thr
225                 230                 235                 240

Phe Met Ala Ile Gly Met Lys Asp Lys Leu Leu Gly Pro Asp Val Met
            245                 250                 255

Tyr Pro Met Lys Ala Leu Ile Asn Gly Cys Pro Glu Pro Leu Glu Ile
            260                 265                 270

Ala Asp Ala Gly His Phe Val Gln Glu Phe Gly Glu Gln Val Ala Arg
            275                 280                 285

Glu Ala Leu Lys His Phe Ala Glu Thr Glu
            290                 295

(2) INFORMATION FOR SEQ ID NO: 8:

(i) SEQUENCE CHARACTERISTICS:
        (A) LENGTH: 329 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (xi) SEQUENCE DESCRIPTION: SEQ ID NO: 8:

```
Phe Ile His Val Lys Pro Pro Gln Leu Pro Ala Gly His Thr Pro Lys
 1               5                  10                  15

Pro Leu Leu Met Val His Gly Trp Pro Gly Ser Phe Tyr Glu Phe Tyr
                20                  25                  30

Lys Ile Ile Pro Leu Leu Thr Asp Pro Lys Asn His Gly Leu Ser Asp
            35                  40                  45

Glu His Val Phe Glu Val Ile Cys Pro Ser Ile Pro Gly Tyr Gly Phe
        50                  55                  60

Ser Glu Ala Ser Ser Lys Lys Gly Phe Asn Ser Val Ala Thr Ala Arg
65                  70                  75                  80

Ile Phe Tyr Lys Leu Met Leu Arg Leu Gly Phe Gln Glu Phe Tyr Ile
                85                  90                  95

Gln Gly Gly Asp Trp Gly Ser Leu Ile Cys Thr Asn Met Ala Gln Leu
               100                 105                 110

Val Pro Ser His Val Lys Gly Leu His Leu Asn Met Ala Leu Val Leu
               115                 120                 125

Ser Asn Phe Ser Thr Leu Thr Leu Leu Gly Gln Arg Phe Gly Arg
130                 135                 140

Phe Leu Gly Leu Thr Glu Arg Asp Val Glu Leu Leu Tyr Pro Val Lys
145                 150                 155                 160

Glu Lys Val Phe Tyr Ser Leu Met Arg Glu Ser Gly Tyr Met His Ile
                165                 170                 175

Gln Cys Thr Lys Pro Asp Thr Val Gly Ser Ala Leu Asn Asp Ser Pro
               180                 185                 190

Val Gly Leu Ala Ala Tyr Ile Leu Glu Lys Phe Ser Thr Trp Thr Asn
               195                 200                 205

Thr Glu Phe Arg Tyr Leu Glu Asp Gly Gly Leu Glu Arg Lys Phe Ser
210                 215                 220

Leu Asp Asp Leu Leu Thr Asn Val Met Leu Tyr Trp Thr Thr Gly Thr
225                 230                 235                 240

Ile Ile Ser Ser Gln Arg Phe Tyr Lys Glu Asn Leu Gly Gln Gly Trp
                245                 250                 255

Met Thr Gln Lys His Glu Arg Met Lys Val Tyr Val Pro Thr Gly Phe
               260                 265                 270

Ser Ala Phe Pro Phe Glu Leu Leu His Thr Pro Glu Lys Trp Val Arg
               275                 280                 285

Phe Lys Tyr Pro Lys Leu Ile Ser Tyr Ser Tyr Met Val Arg Gly Gly
               290                 295                 300

His Phe Ala Ala Phe Glu Glu Pro Glu Leu Leu Ala Gln Asp Ile Arg
305                 310                 315                 320

Lys Phe Leu Ser Val Leu Glu Arg Gln
                325
```

(2) INFORMATION FOR SEQ ID NO: 9:

(i) SEQUENCE CHARACTERISTICS:
    (A) LENGTH: 294 amino acids
    (B) TYPE: amino acid
    (C) STRANDEDNESS: unknown
    (D) TOPOLOGY: unknown (ii) MOLECULE TYPE: peptide (iii) HYPOTHETICAL: NO (xi) SEQUENCE DESCRIPTION: SEQ ID NO: 9:

```
Met Ala Ile Arg Arg Pro Glu Asp Phe Lys His Tyr Glu Val Gln Leu
 1               5                  10                  15

Pro Asp Val Lys Ile His Tyr Val Arg Glu Gly Ala Gly Pro Thr Leu
                20                  25                  30

Leu Leu Leu His Gly Trp Pro Gly Phe Trp Glu Trp Ser Lys Val
            35                  40                  45

Ile Gly Pro Leu Ala Glu His Tyr Asp Val Ile Val Pro Asp Leu Arg
        50                  55                  60

Gly Phe Gly Asp Ser Glu Lys Pro Asp Leu Asn Asp Leu Ser Lys Tyr
65                  70                  75                  80

Ser Leu Asp Lys Ala Ala Asp Gln Ala Ala Leu Leu Asp Ala Leu
                85                  90                  95

Gly Ile Glu Lys Ala Tyr Val Val Gly His Asp Phe Ala Ala Ile Val
                100                 105                 110

Leu His Lys Phe Ile Arg Lys Tyr Ser Asp Arg Val Ile Lys Ala Ala
            115                 120                 125

Ile Phe Asp Pro Ile Gln Pro Asp Phe Gly Pro Val Tyr Phe Gly Leu
        130                 135                 140

Gly His Val His Glu Ser Trp Tyr Ser Gln Phe His Gln Leu Asp Met
145                 150                 155                 160

Ala Val Glu Val Val Gly Ser Ser Arg Glu Val Cys Lys Lys Tyr Phe
                165                 170                 175

Lys His Phe Phe Asp His Trp Ser Tyr Arg Asp Glu Leu Leu Thr Glu
            180                 185                 190

Glu Glu Leu Glu Val His Val Asp Asn Cys Met Lys Pro Asp Asn Ile
                195                 200                 205

His Gly Gly Phe Asn Tyr Tyr Arg Ala Asn Ile Arg Pro Asp Ala Ala
        210                 215                 220

Leu Trp Thr Asp Leu Asp His Thr Met Ser Asp Leu Pro Val Thr Met
225                 230                 235                 240

Ile Trp Gly Leu Gly Asp Thr Cys Val Pro Tyr Ala Pro Leu Ile Glu
                245                 250                 255

Phe Val Pro Lys Tyr Tyr Ser Asn Tyr Thr Met Glu Thr Ile Glu Asp
            260                 265                 270

Cys Gly His Phe Leu Met Val Glu Lys Pro Glu Ile Ala Ile Asp Arg
        275                 280                 285

Ile Lys Thr Ala Phe Arg
        290
```

ENANTIOSELECTIVE EPOXIDE HYDROLASES AND GENES ENCODING THESE

The present invention relates to (microbial) epoxide hydrolases and biocatalytic reactions yielding optically pure epoxides and diols.

Optically active epoxides and 1,2-diols are important building blocks for the production of a range of optically active compounds that are needed for the production of pharmaceuticals and other fine chemicals. A number of strategies are available for the production of optically active epoxides (Schurig et al. 1992). An example that involves a catalytic asymmetric reaction is the Katsuki-Sharpless oxidation of unactivated double bonds, by means of an optically active titanium tartrate complex. A limitation is that the double bond must be in the allylic position relative to the hydroxyl group; this is necessary for coordination of the catalyst. Other procedures for the epoxidation of unfunctionalized prochiral alkenes have been developed using metalated salen- and porphyrin complexes as catalysts (Schurig et al. 1992). These methods have a low selectivity for terminal epoxides and limited applicability due to high catalyst cost and low turnover numbers. In general, the above methods cannot be applied economically on a large scale.

Biocatalytic reactions yielding optically pure epoxides have been described (Beetham et al. 1993; Faber et al, 1996). Lipases can be used for the resolution of racemic esters of epoxyalcohols to produce both enantiomers of the epoxyalcohol. Similarly, lipases may be used for the stereoselective resolution of esters formed from haloalcohols and a carboxylic acid. By transesterification, enantiomerically pure alcohols can be obtained, which may be converted to epoxides.

Biocatalytic production of epoxides is also possible by using mono-oxygenases. These enzymes require an unsaturated substrate and molecular oxygen. Reducing cosubstrates are required, and in general whole cells must be used to make regeneration of the cofactor economically feasible. Haloperoxidase based routes are also known. Haloperoxidases may produce optically active haloalcohols from alkenes.

Enzymatic kinetic resolution is a possible technique for the production of optically active epoxides. Enzymes that hydrolyse epoxides are called epoxide hydrolases. They convert epoxides to diols by cleaving the epoxide ring with water. Epoxide hydrolases have been detected in mammals, insects, yeasts, fungi, other eukaryotic organisms, and in prokaryotic organisms.

The epoxide hydrolases from higher eukaryotic organisms play a role in endogeneous metabolism and do not show strong substrate selectivity. They convert a variety of compounds formed from drugs by oxidative enzymes such as cytochrome P450. The sequence similarity of some epoxide hydrolases to dehalogenases (Beetham et al. 1995, Arand et al. 1994) suggests that they may act by covalent catalysis via a mechanism that does not allow racemisation (Lacourciere et al.,1993; Pries et al., 1994). The epoxide ring is opened by a nucleophilic attack of an carboxylate residue, yielding a covalent ester intermediate. Subsequently this intermediate is hydrolysed and the diol is released.

Production of epoxide hydrolases by eukaryotic organisms is well known. Most work has been done with crude microsomal preparations of liver tissue from rats or other mammals (Wistuba et al. 1992). Mammalian epoxide hydrolases have been studied in detail because epoxides are important in toxicology and in chemical carcinogenesis (Guengerich, 1982). However, the enzymes from mammals, which are known to be stereoselective in some cases, are difficult to obtain and serve multiple functions in vivo.

Styrene oxides are well investigated substrates for microsomal epoxide hydrolases. They have been used in a standard assay for determinaton of the activity of the enzyme. Styrene oxides with substituents on the ring were investigated for studies on the mechanism of this enzyme (Dansette et al. 1978). Further research showed that the microsomal epoxide hydrolase was able to hydrolyse enantioselectivily styrene oxide (Watabe et al. 1983). The time course of this enzymatic hydrolysis showed a biphasic shape. At first the (R)-enantiomer is hydrolysed. After 90% conversion of the (R)-enantiomer, the (S)-enantiomer is hydrolysed at a much faster rate. This behaviour was explained by the fact that the (R)-enantiomer with a smaller $K_m$ could inhibit the hydrolysis of the faster reacting (S)-enantiomer (higher $K_m$, higher $V_{max}$). The enantioselective hydrolysis with mEH was also investigated with p-nitro styrene oxide (Westkaemper et al. 1980) and β-alkyl substituted styrene oxides (Belluci et al 1993 and 1996). Fungal or yeast enzymes are also known and used experimentally. These also are likely to serve detoxification functions or are involved in endogeneous metabolism and are also not very selective. Recently, epoxide hydrolases from *Aspergillus niger* have been used to resolve successfully styrene oxide (Chen et al. 1993) and para substituted styrene oxides such as p-nitro styrene oxide and p-chloro styrene oxide with high enantioselectivity towards the S-enantiomer (Nelliah et al. 1996, Pedragosa-Moreau et al 1996). Another fungus, *Beauveria sulfurescens,* showed high R-selectivity for styrene oxide.

However, production in prokaryotic expression systems of substantial amounts of the epoxide hydrolases that originate from eukaryotes has shown not to be practically feasible. Although many of the above enzymes can be studied experimentally, none of them is available for industrial biocatalytic application. Typical industrial processes which would benefit, however, from the availability of well defined epoxide hydrolases would be the preparation of enantiopure epoxides and 1,2-diols as for example is useful in the production of pheromones and vitamins. Bacterial epoxide hydrolases have been detected in epichlorohydrin-degraders (Nakamura et al. 1994, Jacobs et al. 1991), in organisms that degrade epoxysuccinic acid (Hand et al. 1969), and in organisms that convert nitrils (Hechtberger et al. 1993). The bacterial epoxide hydrolases probably serve a function in the metabolism of endogenous compounds or epoxides produced by monooxygenases, and their selectivitity is not considered high. In a recent review on microbial epoxide hydrolases (Faber et al, 1996) it was observed that epoxide hydrolases could amply been found in eukaryotic cells but were rare in prokayotic cells. However, in some isolates from bacterial genera such as Corynebacterium, Pseudomonas, Bacillus, Mycobacterium and Rhodococcus epoxide hydrolase activity has been observed. Faber et al also described that epoxide hydrolase activity could be induced in only a limited number of bacterial isolates, notably in Rhodococcus spp and in Mycobacterium, whereas isolates from Corynebacterium and Pseudomonas spp did not show any epoxide hydrolase activity and epoxide hydrolase could not be induced by growing these latter species on a selective medium. In addition, Faber et al remark that, although prokaryotic epoxide hydrolases have some advantages above eukaryotic epoxide hydrolases, the enantioselectivities of microbial hydrolases (expressed as enantiomeric ratio (ee)) are low and highly substrate dependent. Faber further remarks, that only a few microbial strains possessing suitable epoxide hydrolase activity for a given substrate are known and prediction of suitable microbial strains is not yet possible, until, for example, the three-dimensional X-ray structure of an epoxide hydrolase has been solved.

The present invention now surprisingly provides isolated micro-organisms that express epoxide hydrolases with a high enantioselectivity. Said micro-organisms represented and provided for by the invention can selectively degrade epichlorohydrin or related halopropanol compounds and their genome encodes a polypeptide having a highly enantioselective epoxide hydrolase activity.

The isolated micro-organism which is the representative micro-organism provided by the invention is Agrobacterium spp exhibiting high enantioselectivity. The micro-organisms provided by the invention essentially correspond to the micro-organism represented by *Agrobacterium radiobacter* deposited under deposit number CBS 750.97. The terms "essentially correspond" or "essentially corresponding" refer to variations that occur in nature and to artificial variations of representative micro-organisms which can selectively degrade epichlorohydrin or related halopropanol compounds and are having enantioselective epoxide hydrolase activity. In particular said variations relate to variations in the epoxide hydrolase and functional fragments thereof which can be isolated from said micro-organisms and to variations in the genome of said organisms encoding epoxide hydrolase and functional fragments thereof. In particular, the terms "essentially correspond" or "essentially corresponding" relate to those variations that still allow detection of epoxide hydrolase or functional fragments thereof in tests for epoxide hydrolase activity or detection of the genome (be it DNA or RNA) or fragments thereof encoding epoxide hydrolase or functional fragments thereof by hybridization techniques, (such as nucleic acid blotting or in situ hybridization) or amplification techniques (such as PCR).

The invention also provides a pure culture of the micro-organism, and a (lyophilized) preparation thereof. The invention also provides a crude or pure enzyme preparation derived from said micro-organism, preparing and purifying enzymes from micro-organisms comprise ordinary skills known in the art. In addition, the invention provides (partly) purified epoxide hydrolase. The enzyme provided by the invention has a molecular weight of 30–40 kD as determined by SDS-polyacrylamide electrophoresis and contains 280–350 amino acids. Epoxide hydrolase as provided by the invention is generally water soluble, generally stable in Tris buffer at neutral pH and is generally able to convert epoxides with a broad specificity. It catalyses the conversion by covalent catalysis, using a nucleophilic aspartate.

The invention now also provides the isolated gene (a recombinant DNA molecule) or parts thereof encoding at least a functional part of a polypeptide having epoxide hydrolase activity. Such genes or fragments thereof can for example be derived from micro-organisms essentially corresponding to those that can selectively degrade epichlorohydrin or related halopropanol compounds.

The invention will be more fully understood by reference to the following detailed description taken in conjunction with the accompanying drawing wherein:

FIG. 1 shows the coding nucleic acid sequence of the gene encoding the epoxide hydrolase of *Agrobacterium radiobacter*, SEQ ID NO: 1;

FIG. 3 shows the sequence alignment of the three dimensional structures of bromoperoxidase A2 and haloalkene dehalogenase;

FIG. 5 is a table showing epoxides containing an aromatic group which can be isolated in enantiomerically pure form by degrading the unwanted enantiomer.

Figure 2:
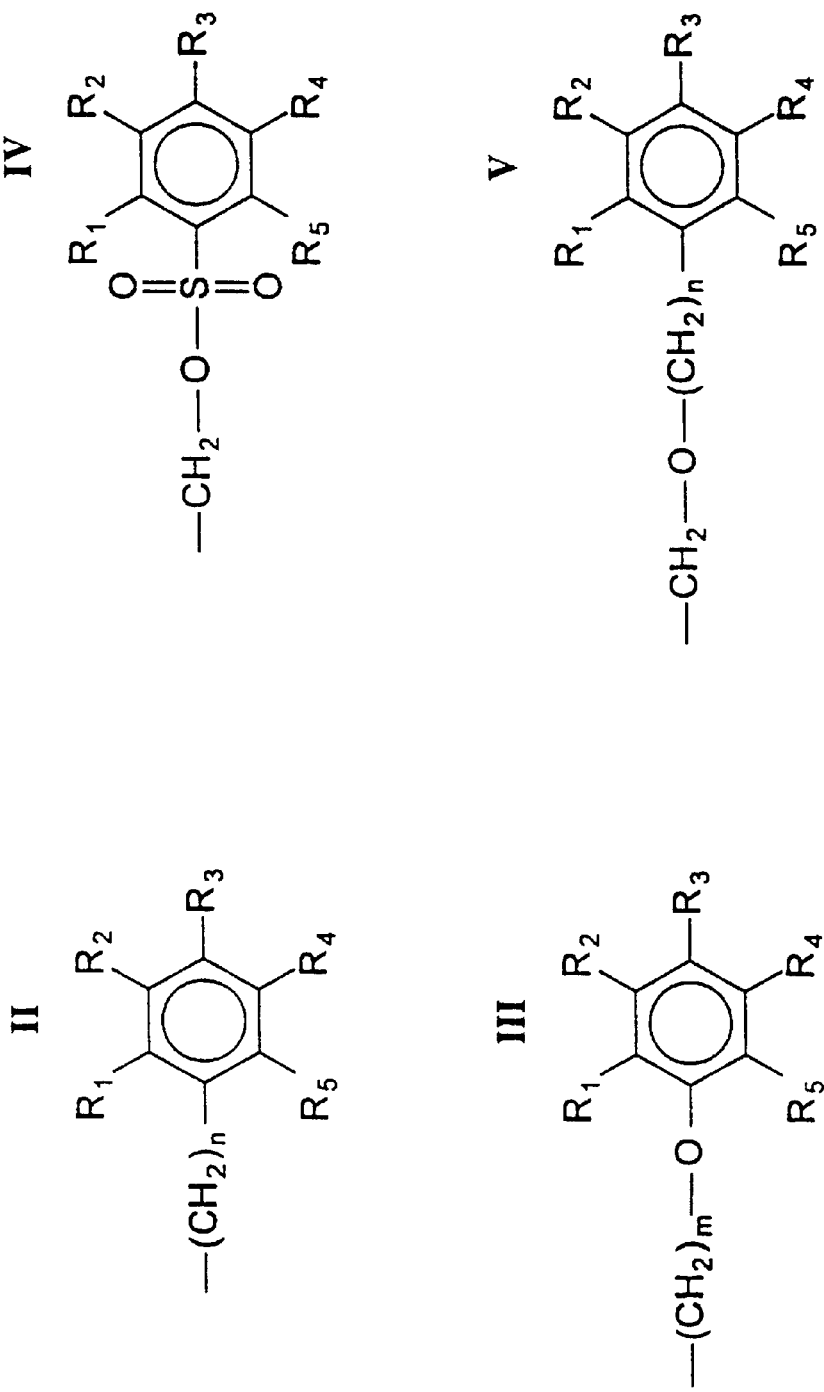
FIG. 2 is a chart showing various epoxides suitable for use in the practice of the present invention.

Furthermore, the invention provides a recombinant DNA molecule encoding a polypeptide exhibiting enantioselective epoxide hydrolase activity. In FIG. 1, the coding nucleic acid sequence of the gene encoding the epoxide hydrolase of *Agrobacterium radiobacter* (deposit number CBS 750.97) is SEQ ID NO: 2.

Furthermore, the invention provides genetically modified epoxide hydrolases with altered epoxide hydrolase activity. Modification is now possible because the functional catalytic site is known. The catalytic site comprises at least the amino acid residues at or around positions 107, 246 and/or 275 of the sequence shown in FIG. 1 SEQ ID NO: 2. The invention provides genomically related epoxide hydrolase in which at least one codon is mutated to encode for an amino acid providing the gene product with a modified epoxide hydrolase activity. Modification is now also possible because the invention provides host cells (such as bacteria or yeast cells, but many host cells are known in the field) that can be transformed via recombinant technology to express epoxide hydrolases and modified versions thereof, and functional fragments thereof. Such host cells can for instance be transformed with a vector comprising a recombinant DNA molecule encoding epoxide hydrolase activity derived from representative micro-organisms that can selectively degrade epichlorohydrin or related halopropanol compounds and which genome encodes a polypeptide having a highly enantioselective epoxide hydrolase activity.

Now that epoxide hydrolase can be produced via recombinant DNA technology, it is possible to obtain it in large quantities in a pure form. This enables for the first time crystallisation of epoxide hydrolase and resolution of its three-dimensional structure, allowing further prediction of microbial strains possessing suitable epoxide hydrolase activity for a given substrate, and allowing further selection of epoxide hydrolases with various selective specificities.

The invention also provides a method of stereoselectively converting racemic mixtures of optically active epoxides to diols, using an epoxide hydrolase obtained from a micro-organism or host cell provided by the invention. The intermediate- and end-products of this conversion are enantiomerically pure epoxides and/or enantiomerically pure diols that can easily be extracted from the reaction mixture by suitable extraction methods known in the art. In said method the reaction can be performed by a pure or semi-pure culture of the micro-organism or by a preparation thereof, or by a crude or pure enzyme preparation derived from said micro-organism or host cell, making industrial application of epoxide hydrolases as biocatalysts in a variety of reactions possible. Immobilized or free enzyme may be used. For immobilisation a wide range of techniques can be applied, for example the absorption of the isolated enzyme or the whole cells onto a water-insoluble macroscopic carrier. Some examples of carriers that can be used are Celite, cellulose, or ion exchange resins such as DEAE-cellulose or DEAE-Sephadex. Another technique is the covalent attachment on an macroscopic carrier such as porous glass or dextran. The isolated enzyme molecules can be crosslinked to each other using a crosslink molecule such as glutardialdehyde. The enzymes can also be entrapped into reversed micelles using an organic solvent and a detergent such as Aerosol OT.

The epoxide hydrolase activity of epichlorohydrin-degrading organisms can be used for the kinetic resolution of mixtures of stereo-isomers of various epoxides, such as styrene oxides or other epoxides containing an aromatic group. These epoxides are represented by the formula given in FIG. 2. An epoxide is allowed to react in the presence of the epoxide hydrolase. After a certain amount is converted, the reaction is stopped and the product is isolated.

The present invention is accordingly also embodied by the process for preparing enantiomerically enriched epoxides and/or diols, comprising contacting a racemic epoxide of the formula

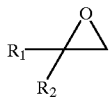

wherein R1 and R2 are independently selected from the group of hydrogen and organic radicals with an isolated micro-organism capable of selectively degrading epichlorohydrin or related halopropanol compounds, said micro-organism being a representative of Agrobacterium spp and comprising a nucleic acid molecule encoding a polypeptide having enantioselective epoxide hydrolase activity.

R1 and R2 are preferably selected from the group of hydrogen and, optionally substituted, straight or branched alkyl, alkenyl, aryl, aralkyl, alkaryl groups.

An enzyme preparation is obtained from the epichlorohydrin-degrading micro-organism Agrobacterium radiobacter or from a recombinant bacterium that expresses an epoxide hydrolase gene obtained from an epichlorohydrin-degrading micro-organism. The epoxide hydrolase gene was cloned by means of the polymerase chain reaction. Based on the N-terminal and C-terminal amino acid sequence, two degenerate primers were designed. Chromosomal DNA was amplified and the resulting 900 bp PCR product was translationally fused in the NcoI-(startcodon)-site of pGEF+, resulting in pEH20. The gene is under control of the strong T7 promotor and typically 100–200 mg of purified epoxide hydrolase can be obtained from one liter of culture of E.coli BL21. The f1 origin of replication makes it a suitable mutagenesis and sequence vector. The epoxide hydrolase is produced by growing a host cell in a fermentor under conditions which cause expression. Both constitutive production or induced production of the enzyme is possible. Alternatively, the DNA encoding for the epoxide hydrolase of an epichlorohydrin degrading bacterium is cloned into an expression vector by PCR amplification and cloning of the amplified DNA or by cloning of restriction enzyme fragments. The cloned DNA is expressed by induction or by stimulating expression of a specific polymerase. Subsequently, the epoxide hydrolase is produced under standard conditions.

Figure 3:
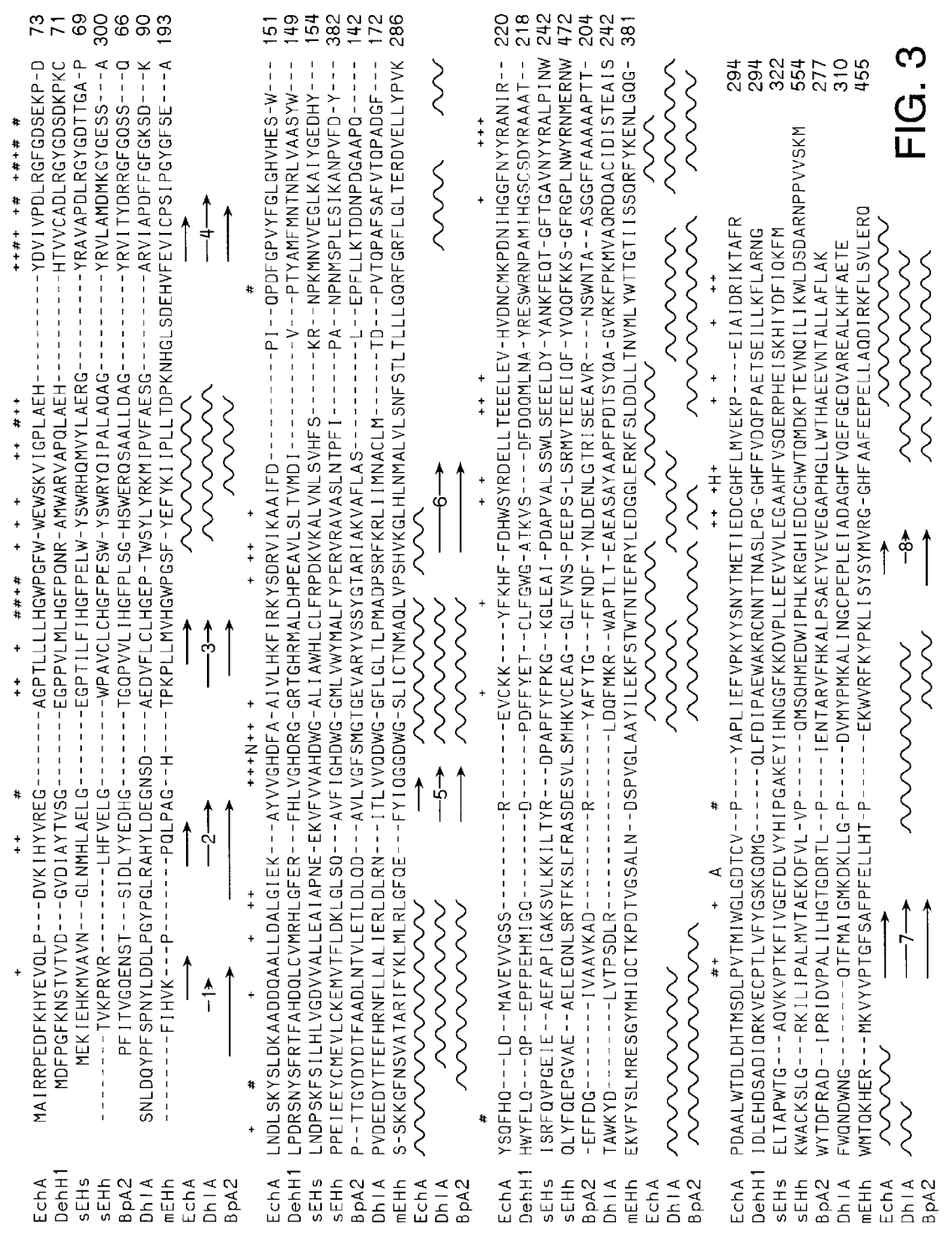

The epoxide hydrolase is remarkably similar to haloalkane dehalogenase from Xanthobacter autotrophicus GJ10, both in structure and reaction mechanism. Based on homology, we classify this enzyme as an α/β hydrolase fold enzyme. The catalytic triad residues (Asp$^{107}$-His$^{275}$-Asp$^{246}$) are identified by sequence similarity and by mutation. Further it is shown that the reaction mechanisms of epoxide hydrolase proceeds via a covalently bound ester intermediate. The three dimensional structures of bromoperoxidase A2 and haloalkane dehalogenase are solved and their structural elements are displayed in the sequence alignment in FIG. 3,. Also the consensus of four secondary structure prediction programs for epoxide hydrolase is shown.

Clearly, the predicted structural elements of the main domain coincide. The sequence alignment shows that the catalytic residues of bromoperoxidase A2 and haloalkane dehalogenase are also conserved in epoxide hydrolase (marked by D and H).

Figure 4:
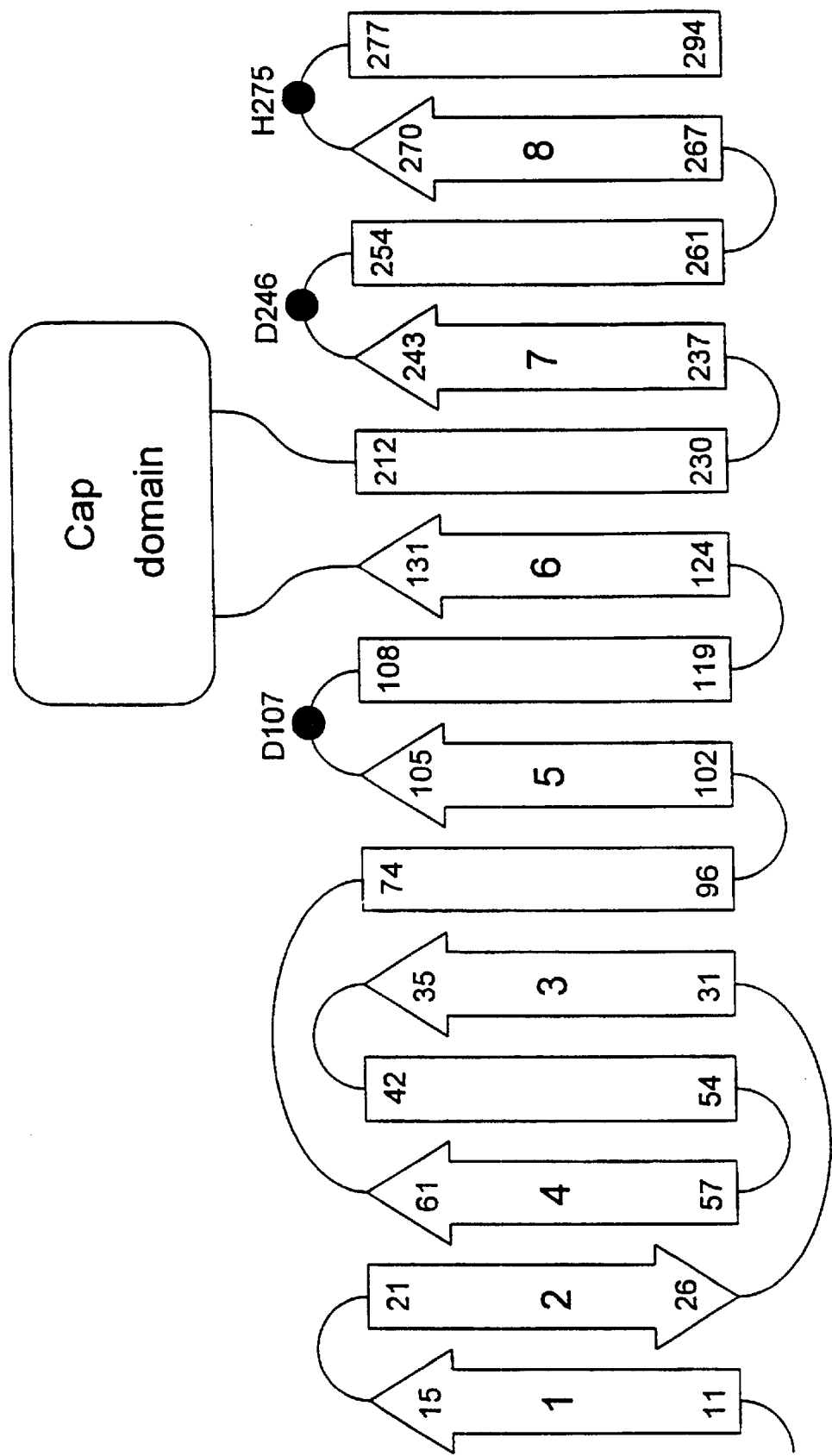
FIG. 4 is a ploy showing the topology of the α/β-hydrolase fold of bromoperoxidase A2 and haloalkane dehalogenase.

The plot in FIG. 4 shows the topology of the α/β-hydrolase fold of bromoperoxidase A2 and haloalkane dehalogenase. The main domain consists out of a central β-sheet surrounded by α-helices. The cap domain is formed out of α-helices and is specific for each enzyme. The catalytic triad residues, the nucleophile (D107), histidine (H275), and the acid residue (D246) occupy preserved positions in the topology.

Sequence similarity studies pointed out the residues Asp107, His275, and Asp246 as the catalytic residues of epoxide hydrolase, i.e. the functional part thereof. Mutants were constructed to support this hypothesis. All mutant enzymes were expressed in crude extract as soluble enzyme and in quantities comparable to wild type epoxide hydrolase. Steady state activities were determined in crude extract. Asp107Ala, Asp107Glu, His275Arg and His275Glu mutants were not catalytically active, only the Asp246Ala mutant had residual activity left.

Single turnover experiments with the mutant His275Arg enzyme and epichlorohydrin which were quenched after different reaction times showed that epichlorohydrin disappeared within seconds without the formation of product. We conclude that the diol formed from epichlorohydrin is covalently bound to the enzyme.

The reaction that we postulate but that in no way can be seen as limiting the invention for epoxide hydrolase is as follows. Asp$^{107}$ performs a nucleophilic attack on the primary carbon atom of the epoxide ring. Incorporation of $^{18}$O labelled water occurs only at the primary carbon atom. A water molecule that is activated by His$^{275}$ attacks the carbonyl function of Asp$^{107}$, and product is released. Asp$^{246}$ has a charge relay function. In analogy with Trp$^{125}$ in haloalkane dehalogenase, Phe$^{108}$ could be involved in substrate binding. We also expect the presence of a proton donor group, located in the cap domain.

In conclusion, the epoxide hydrolase of Agrobacterium spp. belongs to the class of α/β-hydrolase folded enzymes. The displayed sequence similarity, the structural features (secondary structure prediction and circular dichroism), the inactive active site mutants, and the existence of an ester intermediate are all in agreement.

It is now possible to study the kinetics of epoxide hydrolase by performing rapid quench and stopped flow experiments. Stopped flow experiments are possible since substrate is able to quench the fluorescence signal of some of the tryptophans present in epoxide hydrolase. Also, it is possible to mutate (replace) the amino acids (e.g. tryptophans) that are involved in substrate binding. Either with site-directed mutagenesis or random mutagenesis, it is possible to modify the substrate specificity and the stereoselectivity of epoxide hydrolase. The epoxide hydrolase has the following characteristics.

34 kDa monomeric enzyme (approximately 294 amino acids)

high expression in E.coli and stable at 4° C. for at least half a year epoxide hydrolase contains considerable amounts of α-helical and β-stranded structure as is demonstrated by Circular Dichroism epichlorohydrin is a suitable substrate ($V_{max}$=25 μmol min$^{-1}$.mg.protein$^{-1}$, $K_m$<30 μM)

Its DNA sequence is shown in FIG. 1. It is generally soluble, generally stable in Tris buffer at neutral pH and is able to convert several epoxides with a broad specificity. The epoxide hydrolase is isolated and used directly or stored as a lyophilised preparation. For lyophilization, the enzyme is dialysed against a suitable buffer. Immobilised or free enzyme may be used.

The asymmetric hydrolysis of the substrate is generally conducted in aqueous solution. The pH of the solution is maintained by means of a buffer. Maximum enzyme activity is obtained at pH 9 but a range of pH 5 to 11 can be employed. The composition of the buffer can for example be Tris/$H_2SO_4$, potassium phosphate or glycine/NaOH. The maximum enzyme activity is obtained at a temperature of 50° C., but the reaction can be conducted at a temperature ranging from 5° C. to 65° C. The substrate concentration used to measure the enzyme activity is from 1 to 20 mM. In case of poorly soluble substrates, the water solubility can be increased by adding a miscible organic cosolvent such a DMSO. Also other organic solvents can be used. Generally a higher cosolvent concentration increases the maximum solubility of the substrate, but it must not be so high as to inactivate the enzyme. The epoxide can also be introduced as a second phase. This can either be done by dissolving the epoxide in a non-miscible organic solvent such as octane or the epoxide itself can be added, as a liquid or a solid. This is then brought into contact with an aqueous phase containing the enzyme and the two phases are subsequently vigorously mixed. After completion of the reaction, the epoxide can easily be recovered or obtained from the organic solvent.

In a typical experiment, the substrate is dissolved in a quantity of buffer, with or without cosolvent, to a concentration of 1 mM to 250 mM. The lyophilised enzyme preparation is dissolved in a small quantity of buffer and is allowed to stabilise for some time. The enzyme solution is subsequently mixed with the buffer solution. The reaction is monitored by analysis of the degree of conversion of the epoxide or by appearance of the product of the conversion, the diol. This is determined by sampling a part of the reaction liquid and extracting it with an appropriate organic solvent. For the extraction of the epoxides diethyl ether can for example be used and for the diol ethylacetate can for example be used.

The enantiomeric composition of the epoxides is determined by a gaschromatography using a chiral column such as CP-cyclodextrin-b2,3,6-M19. Using the epoxide hydrolase, a large number of epoxides containing an aromatic group can be isolated in enantiomerically pure form by degrading the unwanted enantiomer. This can be done for e.g. styrene oxide, p-methylstyrene oxide, x-methylstyrene oxide, fenylglycidyl ether, and glycidyl tosylate (FIG. 5). The enantiomerically pure product may be used for the synthesis of various other optically active compounds.

EXAMPLE 1

The production of styrene oxide with recombinant epoxide hydrolase *Agrobacterium radiobacter* strain AD1 expressed in *E.coli*. The epoxide hydrolase gene was cloned by means of PCR by using degenerate primers that were designed on the amino acid sequence of the N-terminus and the C-terminus that was known from publication in literature. Total DNA of *Agrobacterium radiobacter* strain AD1 was isolated from cells cultivated on 1,3-chloro-2-propanol using standard procedures. The gene of interest was amplified and cloned in an expression vector behind a T7-promotor of a plasmid such as PGEF, and brought to expression in *E.coli*. The recombinant enzyme was produced by fermentation. The whole cells were subsequently lyophilised or a crude cell-free extract was prepared by ultrasonic disruption and centrifugation of the cells followed by a purification step with an anion exchange column. Finally the extract was dialysed against a Tris-buffer, lyophilised and stored at 4° C.

Prior to use the lyophilised cell-free extract (0.50 mg) was suspended in Tris buffer (pH 9.0, 50 mM, 0.5 ml). A flask containing a solution of 5 mM styrene oxide in Tris buffer (pH 9.0, 50 mM, 20 ml) was incubated at 30□ C. and the previously prepared enzyme solution was added. After 50 minutes the reaction was stopped and the remaining styrene oxide was extracted with diethyl ether. The enantiomeric purity of the styrene oxide was determined by chiral gas chromatography on a β-cyclodextrin phase (CD-cyclodextrin-b-2,3,6-M-19) at 95° C. The remaining (S)-enantiomer of the styrene oxide had an e.e. of 99% and a yield of 65%.

EXAMPLE 2

An amount of the lyophilised cell-free extract (4.5 mg) was suspended in Tris buffer (pH 9.0, 50 mM, 1 ml). A flask containing a solution of 5 mM phenyl glycidyl ether in Tris buffer (pH 9.0, 50 mM, 100 ml) was incubated at 30° C. and the prepared enzyme solution was added. After 15 minutes the reaction was stopped and the remaining epoxide was extracted with diethyl ether. The enantiomeric purity of the remaining (R)-enantiomer was determined by chiral gas chromatography using a cyclodextrin column. The remaining (R)-enantiomer of the phenyl glycidyl ether had an e.e. >99% and a yield of 55%.

EXAMPLE 3

An amount of the lyophilised cell-free extract (0.7 mg) was suspended in Tris buffer (pH 9.0, 50 mM, 1 ml). A flask containing a solution of 5 mM para-chlorostyrene oxide in Tris buffer containing 10% DMSO (pH 9.0, 50 mM, 20 ml) was incubated at 30° C. and the prepared enzyme solution was added. After 15 minutes the reaction was stopped and the remaining para-chlorostyrene oxide was extracted with diethyl ether. The remaining (S)-enantiomer of the para-chlorostyrene oxide had an e.e. >99% and a yield of 67%.

EXAMPLE 4

An amount of the lyophilised whole recombinant cells (5 mg) was suspended in Tris buffer (pH 9.0, 50 mM, 1 ml). A flask containing a solution of 5 mM styrene oxide in Tris buffer (pH 9.0, 50 mM, 100 ml) was incubated at 30° C. and the prepared whole cell suspension was added. After 65 minutes the reaction was stopped and the remaining styrene oxide was extracted with diethyl ether. The remaining (S)-enantiomer of the styrene oxide had an e.e. of 99% and a yield of 56%.

EXAMPLE 5

An amount of the lyophilised cell-free extract (100 mg) was suspended in Tris buffer (pH 9.0, 50 mM, 10 ml). A flask containing a solution of 50 mM styrene oxide in Tris buffer with 20% (v/v) DMSO (pH 9.0, 50 mM, 1000 ml) was incubated at 30° C. and the prepared enzyme solution was added. After 125 minutes the reaction was stopped and the remaining styrene oxide was extracted with diethyl ether. The remaining (S)-styrene oxide had an e.e. >99% and a yield of 60%.

EXAMPLE 6

An amount of the lyophilised cell-free extract (25 mg) was suspended in Tris buffer (pH 9.0, 50 mM, 1 ml). A flask containing a solution of 5 mM glycidyl tosylate in Tris buffer with 10% (v/v) DMSO (pH 9.0, 50 mM, 100 ml) was incubated at 30° C. and the prepared enzyme solution was added. After 20 minutes the reaction was stopped and the remaining epoxide was extracted with diethyl ether. The remaining (R)-enantiomer of the glycidyl tosylate had an e.e. >99% and an analytical yield of 45%.

Figure Legends

FIG. 1

Complete DNA and amino acid sequence of the epichlorohydrin epoxide hydrolase gene echA from *Agrobacterium radiobacter* deposited at the Centraalbureau voor Schimmelcultures under number CBS 750.97. The residues shown at amino acid position 107, 246 and 275 comprise catalytic residues of epoxide hydrolase SEQ ID NO: 1 and SEQ ID NO: 2.

FIG. 2

Substrate for epoxide hydrolase I, wherein $X_1$ is represented by II, III, IV or V and $X_2$, $R_1$, $R_2$, $R_3$, $R_4$ and $R_5$ are independent from each other and may be chosen from among a hydrogen atom, a halogen atom, a nitro group, an alkyl group, a hydroxyl group, or a cyanide group. The length of the aliphatic chain can be n=0,1,2 or 3 and m=1,2 or 3.

FIG. 3

Sequence alignment of EchA with other hydrolases. The sequences were aligned using the multiple alignment program ClustalW and are shown in order of sequence similarity to the epoxide hydrolase cloned in this study. Six conserved amino acids are marked with #, four or five conserved residues are marked with +. The nucleophile is marked by N, the catalytic histidine by H, and the catalytic acid residue by A. Below the sequence alignment, the predicted secondary structure elements of EchA, and the determined secondary structures of Dh1A and BpA2 are shown. β-Strands are shown as arrows (numbered as for Dh1A) and α-helices are shown as waves. Sequences: EchA, epoxide hydrolase from *A. radiobacter* strain AD1 SEQ ID NO: 2; DehH1, fluoracetic acid dehalogenase from Moraxella sp. strain B SEQ ID NO: 3; sEHs, soluble epoxide hydrolase from potato SEQ ID NO: 4; sEHh, soluble epoxide hydrolase from human SEQ ID NO: 5; BpA2, bromoperoxidase A2 from *Streptomyces aereofaciens* SEQ ID NO: 6; DH1A, haloalkane dehalogenase from *Xanthobacter autotrophicus* SEQ ID NO: 7 GJ10 and MeHh, microsomal epoxide hydrolase from human SEQ ID NO: 8.

FIG. 4

Topology of the α/β hydrolase fold of epoxide hydrolase from *Agrobacterium radiobacter*. Arrows indicate β-strands, boxes indicate a-helices. The numbers printed in large font indicate β-strands, those in small font indicate the residue numbers according to the amino acid sequence. The positions of the three catalytic triad residues is indicated.

FIG. 5

Kinetic resolution of aromatic epoxides by epoxide hydrolase from *Agrobacterium radiobacter* a) determined by injection of optically pure compound b) determined by optical rotation c) in 10% DMSO.

REFERENCES

Arand M., Grant D. F., Beetham J. K., Friedberg T., Oesch F., Hammock B. D. (1994). *FEBS Lett.* 338, 251–256.

Archer, I. V. J. (1997), Tetrahedron, 53, 15617–15662

Beetham J. K., Grant D., Arand M., Garbarino J., Kiyosue T., Pinot F., Oesch F., Belknap W. R., Shinozaki K., Bont, J. A. M. de. (1993) *Tetr. Asymm.* 6, 1331–1340.

Watabe, T., Ozawa, N., Hiratsuka, A. (1983) *Biochem. Pharm.* 32, 777–785

Chen, X. J., Archelas, A., Furstoss, R. (1993) *J. Org. Chem.* 58, 5528–5532, and 5533–5536.

Nelliah, H., Morisseau, C., Archelas, A, Furstoss, R, Baratti, J. C. (1996) *Biotech. Bioeng.* 49, 70–77.

Nakamura, T, Nagasawa, T, Yu, F., Watanabe, I., Yamada, H. (1994) *Appl. Environ. Microbiol.* 12, 4630–4633

Pedragosa-Moreau, S., Morisseau, C., Zylber, J., Archelas, A., Baratti, J., Furstoss, R. (1996) *J. Org. chem.* 61, 7402–7407

Guengerich, F. P. (1982) *Rev. Biochem. Toxicol.* 4, 5–30.

Beetham, K. B., Grant, D., Arand, M., Garbarino, J., Kiyosue, T., Pinot, F., Oesch, F., Belknap, W. R., Shinozaki, K., Hammock B. D. (1995) *DNA Cell Biol* 14, 61–71.

Hechtberger, P., Wirnsberger, G., Mischitz, M., Klempier, N., Faber, K. (1993). *Tetr. Asymm.* 4, 1161–1164.

Jacobs, M. H. J., A. J. van den Wijngaard, M. Pentenga, D. B. Janssen. (1991). *Eur. J. Biochem.* 202, 1217–1222.

Lacourciere, G. M., Armstrong, R. N. (1993) *J. Am. Chem. Soc.* 115, 10466–10467.

Hand, R. H., Jakoby, W B. (1969) *J.Biol. Chem.* 244, 2078–2084.

Pinot, F., Grant, D. F., Beetham, J. K., Parker, A. G., Borhan, B., Landt, S., Jones, A. D., Hammock B. D. (1995) *J Biol Chem* 270, 7968–7974.

Pries, F., Kingma, J., Pentenga, M., .van Pouderoyen, G., Jeronimus-Stratingh, C. M., Bruins, A. P., Janssen. D. B. (1994) *Biochemistry* 23, 1242–1247.

Dansette, P. M., Makedonska, V. B., Jerina, D. M. (1978) Arch. Biochem. Biophys. 2, 290–298.

Westkamper, R. B., Hanzlik, R. P. (1981) Arch. Biochem. Biophys. 208, 195–204.

Schurig, V., Betschinger, F. (1992) *Chem. Rev.* 92, 873–888.

Swaving J. et al. 1994. *Biocatalysis* 10, 227–232.)

Wistuba, D., Schurig, V. (1992). *Chirality* 4, 178–184.

Belluci, G., Chiappe, C., Cordoni A., Marioni, F. (1993) *Tetr. Asymm.* 4, 1153–1160.

Belluci, G., Chiappe, C., Cordoni A. (1996) 7, 197–202.

Faber et al., actu.chem.Scand.(1996) 50, 249–258

We claim:

1. A crude or pure enzyme preparation comprising an isolated polypeptide or functional fragments thereof, having epoxide hydrolase activity, said polypeptide derived from a micro-organism being a representative of Agrobacterium spp and comprising a nucleic acid molecule encoding a polypeptide having enantioselective epoxide hydrolase activity.

2. An isolated polypeptide or functional fragments thereof, having epoxide hydrolase activity, said polypeptide or a fragment thereof derived from a micro-organism according to claim 1.

3. An isolated polypeptide having enantioselective epoxide hydrolase activity, said polypeptide having a catalytic mechanism based on a catalytic triad formed by two aspartate and one histidine groups, as defined in FIG. 1 (SEQ ID NO: 2).

4. An isolated polypeptide according to claim 2, having an amino acid sequence that corresponds for at least 90% to the sequence of FIG. 1 (SEQ ID NO: 2).

5. A method for producing an isolated polypeptide or a fragment thereof having epoxide hydrolase activity comprising the use of a microorganism being a representative of Agrobacterium spp and comprising a nucleic acid molecule encoding a polypeptide having enantioselective epoxide hydrolase activity, or a host cell for expression of a polypeptide or a fragment thereof having epoxide hydrolase activity.

6. A crude or pure enzyme preparation, comprising an isolated polypeptide or functional fragments thereof, having epoxide hydrolase activity, said polypeptide being derived from a host cell for expression of a polypeptide or a fragment thereof having epoxide hydrolase activity derived from Agrobacterium spp.

7. An isolated polypeptide or a fragment thereof having epoxide hydrolase activity obtainable by a method according to claim 5.

8. An isolated polypeptide or a fragment thereof according to claim 7, wherein said polypeptide exhibits enantioselective activity.

9. Method for stereoselectively converting racemic mixtures of optically active epoxides to diols which comprises reacting said mixture with an epoxide hydrolase obtained from a micro-organism which is a representative of Agrobacterium spp and comprising a nucleic acid molecule encoding a polypeptide having enantioselective epoxide hydrolase activity.

10. Method for stereoselectively converting racemic mixtures of optically active epoxides to diols which comprises reacting said mixture with a host cell for expression of a polypeptide or a fragment thereof having epoxide hydrolase activity derived from Agrobacterium spp.

11. Method for the preparation of enantiopure epoxides and diols which comprises contacting a racemic epoxide with an isolated microorganism which is a representative of Agrobacterium spp and comprising a nucleic acid molecule encoding a polypeptide having enantioselective epoxide hydrolase activity.

* * * * *